(12) United States Patent
Hanks et al.

(10) Patent No.: US 12,077,738 B2
(45) Date of Patent: Sep. 3, 2024

(54) SYSTEMS AND METHODS COMPRISING OPEN ALGAE CULTIVATION LINERS

(71) Applicant: ExxonMobil Technology and Engineering Company, Annandale, NJ (US)

(72) Inventors: Patrick L. Hanks, Bridgewater, NJ (US); Louis R. Brown, La Jolla, CA (US); Everett J. O'Neal, Asbury, NJ (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 511 days.

(21) Appl. No.: 17/198,482

(22) Filed: Mar. 11, 2021

(65) Prior Publication Data
US 2021/0371787 A1 Dec. 2, 2021

Related U.S. Application Data

(60) Provisional application No. 63/032,763, filed on Jun. 1, 2020.

(51) Int. Cl.
*C12M 1/00* (2006.01)

(52) U.S. Cl.
CPC ............ *C12M 23/18* (2013.01); *C12M 21/02* (2013.01)

(58) Field of Classification Search
CPC ....... C12M 23/18; C12M 21/02; A01G 33/00; E04H 4/0018; E04H 2004/0068; E02B 3/126; E02B 13/00; E02D 31/004
See application file for complete search history.

(56) References Cited

U.S. PATENT DOCUMENTS

| 5,139,853 A * | 8/1992 | Mathieson | .............. E02D 31/00 428/131 |
| 2013/0061450 A1* | 3/2013 | Wherley | .................. E04H 4/14 29/525.01 |

FOREIGN PATENT DOCUMENTS

WO WO-9426793 A1 * 11/1994 .............. C08F 10/00

OTHER PUBLICATIONS

Dodd, Joseph C., "Elements of Pond Design and Construction", 1986, CRC Press, 1st Edition (Year: 1986).*

* cited by examiner

*Primary Examiner* — Elizabeth A Robinson
*Assistant Examiner* — Jonathan E Lepage
(74) *Attorney, Agent, or Firm* — Shook, Hardy & Bacon L.L.P.

(57) ABSTRACT

The present disclosure relates to algae cultivation including the integration of liners for large-scale open algal biomass to facilitate algae facility commercial scale-up operations. Liners include those having a first portion having a first thickness and a second portion comprising a second thickness, wherein the first thickness and the second thickness are different. Liners also include those having a first portion having a first thickness, a second portion comprising a second thickness, and a third portion comprising a third thickness, wherein the first thickness, the second thickness, and the third thickness are different.

18 Claims, 2 Drawing Sheets

SYSTEMS AND METHODS COMPRISING OPEN ALGAE CULTIVATION LINERS

CROSS-REFERENCE TO RELATED APPLICATIONS

This application is related to and claims the benefit of priority from U.S. Provisional Application No. 63/032,763 filed Jun. 1, 2020, which is hereby incorporated by reference in its entirety.

FIELD OF THE INVENTION

The present disclosure relates to algal biomass cultivation.

BACKGROUND OF THE INVENTION

Concerns about climate change, carbon dioxide ($CO_2$) emissions, and depleting mineral oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources.

Algae are photoautotrophic organisms that can survive, grow, and reproduce with energy derived entirely from the sun through the process of photosynthesis. Photosynthesis is essentially a carbon recycling process through which inorganic $CO_2$ combines with solar energy, other nutrients, and cellular biochemical processes to output gaseous oxygen and to synthesize carbohydrates and other compounds critical to the life of the algae.

To produce algal biomass in outdoor environments, algae is generally grown in a water slurry using one or more open cultivation vessel systems, which are typically oval in shape (e.g., pill-shaped) and referred to as "raceway ponds." The algae water slurry comprises selected nutrients and the open cultivation system circulates the algae in the water slurry to ensure adequate exposure to solar energy, thereby promoting the growth of algal biomass. Various downstream processing methods are used to separate the algal biomass and extract lipids therefrom for the production of biofuel and other oil-based (and non-oil-based) products, including nutraceuticals, pharmaceuticals, cosmetics, chemicals (e.g., paints, dyes, and colorants), fertilizer and animal feed, and the like. The remaining wastewater and biomass residue can be recycled or otherwise used in a variety of sustainable applications. For example, the wastewater can form some or all of a subsequent water slurry and the biomass residue can be used as animal feed.

Because the processing of algal biomass produces valuable commodities, including sustainable biofuels, large-scale cultivation of algae is desirable. Various engineering complications may be associated with scaling an algae cultivation process, such as designing linings that protect circulating algae slurries in open cultivation vessels and allowing for access to such vessels for cleaning and other maintenance activities. Traditionally, open cultivation vessels are clay lined or plastic lined to ensure that the algae water slurry is maintained within the vessel should any leak or other compromise occur as the slurry is circulating. However, these traditional liners may be ineffective, cost prohibitive, or otherwise problematic.

Moreover, to compete merely with U.S. diesel demand, a single algae biofuel facility would likely need to produce at least 10 thousand barrels per day (kbd), or even more (e.g., 20 kbd), to be viable, which is on par with current refinery facilities producing petroleum products. Accordingly, the total area of an open vessel system for true commercial algal biomass cultivation would need to be extremely large, requiring large vessels covering hundreds, or even thousands, of total surface area acreage.

SUMMARY OF THE INVENTION

The present disclosure relates to algal biomass cultivation and, more particularly, to large-scale open algal biomass cultivation vessel liners.

In one or more aspects, the present disclosure provides a joined liner for lining an open algae cultivation vessel. The joined liner includes a first portion having a first thickness and a second portion comprising a second thickness. The second thickness is at least about 1.5 times greater than the first thickness.

In one or more aspects, the present disclosure provides a joined liner for lining an open algae cultivation vessel. The jointed liner includes a first portion having a first thickness, a second portion comprising a second thickness, and a third portion comprising a third thickness. The first thickness, the second thickness, and the third thickness are different and the second thickness is at least about 1.5 times greater than the first thickness.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1:
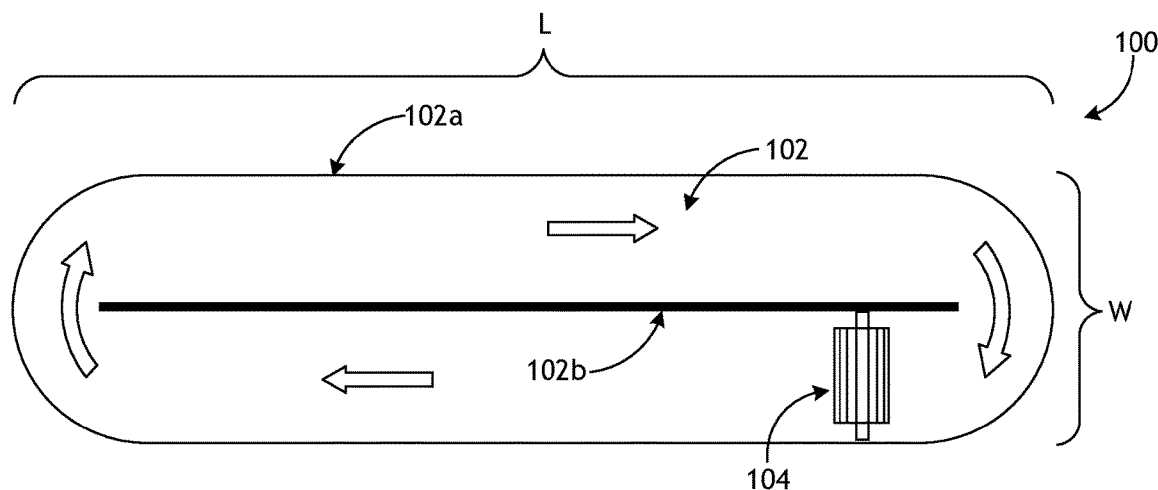
FIG. 1 is a schematic illustration of a top-view of a standard raceway pond open algae cultivation vessel.

The present disclosure relates to algal biomass cultivation and, more particularly, to large-scale open algal biomass cultivation vessel liners.

Biofuel production from cultivated algae slurries offers sustainable energy solutions to reduce reliance on fossil fuels and reduce greenhouse gas emissions. Generally, algae slurries are cultivated in open cultivation vessels (e.g., outdoor raceway ponds) that are clay or plastic lined to contain circulating slurries therein. These open cultivation vessels tend to be traditionally on the order of one or two acres in size. However, to accomplish substantial economic, environmental, and societal impact, algae must be cultivated in large-scale systems, with open vessels being on the order of 5 to 20 acres in size or greater, for example. Such large-scale cultivation systems further allow algae-derived fuels to become more cost-effective and more widely available to the public by enlarging production quantities without compromising productivity or quality. Successful scale-up is vital to the commercial viability of an algae cultivation facility, in terms of at least both operational cost control and algal product quantity. Moreover, successful scale-up is vital to ensure that a facility is achieving desirable production rates (e.g., those that can enable commercial viability). At present, no methodology for optimizing liners for use in open algae cultivation vessels is currently available to those of skill in the art to account for algae facility scale-up. Rather, single material, single thickness liners are used regardless of the algae vessel size or algae facility footprint.

The present disclosure provides for optimizing open cultivation algae vessel lining systems to protect and service cultivating algae, which beneficially also permits reduced facility footprint without a reduction in the amount or quality of algae-produced products manufactured therefrom (e.g., biofuel).

As used herein, the term "algae slurry" or "algae water slurry," and grammatical variants thereof, refers to a flowable liquid comprising at least water, algae cells, and algae nutrient media (e.g., phosphorous, nitrogen, and optionally additional elemental nutrients).

Algal sources for preparing the algae slurry include, but are not limited to, unicellular and multicellular algae. Examples of such algae can include, but are not limited to, a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

The water for use in preparing the algae slurry may be from any water source including, but not limited to, fresh water, brackish water, seawater, wastewater (treated or untreated), synthetic seawater, and any combination thereof.

The algae nutrient media for use in forming an algae slurry may comprise at least nitrogen (e.g., in the form of ammonium nitrate or ammonium urea) and phosphorous. Other elemental micronutrients may also be included, such as potassium, iron, manganese, copper, zinc, molybdenum, vanadium, boron, chloride, cobalt, silicon, and the like, and any combination thereof.

As used herein, the term "open cultivation vessel," "vessel," and grammatical variants thereof, refers to any of an open, outdoor algae cultivation system used for the growth of algal biomass, including natural ponds, artificial ponds (e.g., raceway ponds), and the like, including combinations thereof. While the embodiments of the present disclosure are generally described with reference to raceway pond algae cultivation vessels, it is to be appreciated that any open cultivation vessel system may be used in accordance with the embodiments of the present disclosure. Accordingly, the terms "open cultivation vessel" and "raceway pond" or "pond," and grammatical variants thereof, will be used interchangeably herein.

As used herein, the term "algae liner," "cultivation vessel liner," "liner," and grammatical variants thereof, refers to a covering protecting at least a portion of an open algae cultivation vessel or protecting access to at least a portion of an open algae cultivation vessel, such as an interior (or inside) bottom surface, an interior side wall (e.g., protecting from erosion and organic growth), or an edge surface proximate to an interior wall surface of the vessel (e.g., an earthen berm from which the vessel was constructed). It is to be understood that ponds dug into the Earth's surface will have an interior side wall that rises to the Earth's surface and is contiguous with adjacent berms; proximate portions of said berms may be, but need not be, structurally supported, such as with a concrete or stone surface coating, for example. Further, ponds dug into the Earth's surface typically comprise an interior bottom surface of compacted earth, which may have a geotextile atop the compacted earth. The liners described herein may, in one or more aspects, cover said compacted earth or said geotextile, without departing from the scope of the present disclosure. When the liner covers a geotextile, the geotextile may provide support and/or buffering to the liner while the liner contains an algae slurry. In one or more aspects, multiple algae liners may be used in accordance with the present disclosure (e.g., of differing thickness, composition, and the like) to provide protection while optimizing large-scale cultivation systems, which are polymeric in composition and may be separate or otherwise joined together (e.g., welded, fused, glued, or otherwise connected). That is, a joined liner comprised of multiple liners (e.g., of differing thickness, composition, and the like) is encompassed in the term "algae liner."

For purposes of the present disclosure, the various systems and methods of the present disclosure will be described with reference to open cultivation vessel raceway ponds. Accordingly, before describing various specific aspects of the present disclosure in detail, a brief overview of standard open algae cultivation raceway ponds that may be utilized in accordance with one or more embodiments of the present disclosure is provided with reference to FIG. 1. As illustrated in FIG. 1, raceway pond 100 is a single closed-loop, oval-shaped (e.g., pill-shaped) pond having recirculation channel 102. Raceway pond 100 may be artificial and shallow, typically designed to circulate an algae slurry at a depth of no greater than about 14 inches to facilitate sufficient sunlight penetration needed for algae growth.

The recirculation channel 102 is defined by interior side walls 102a and separating divider 102b. Interior side walls 102a may be formed from naturally-occurring earth material at the location of the pond 100 (e.g., berm materials of soil, clay, compacted sand, or other earth materials from forming or digging the recirculation channel 102) or other structural materials (e.g., a concrete material, a metal material, a polymeric material, and the like) whether the pond 100 is below ground or above-ground. That is, the structural material may be used to provide structural stability to below ground earthen material dug to form pond 100 or to provide structural stability to an above-ground pond 100, without departing from the scope of the present disclosure. Similar structural materials may also be used to form the separating divider 102b (whether of the same or to different structural material of the side wall 102a, when applicable).

As shown, raceway pond 100 has a length ("L") and a width ("W"). A typical (non-scaled-up) raceway pond may, for example, have a length to width ratio of greater than about 10:1 and generally cover one or two acres of surface area (e.g., a one acre raceway pond may have a length of about 650 feet and a width of about 38 feet). Further, although raceway pond 100 is shown having a single closed-loop, oval-shaped recirculation channel 102, in other aspects, a suitable raceway pond may have multiple closed-loop, oval-shaped recirculation channels, or may comprise other shaped recirculation channels, without departing from the scope of the disclosure.

With continued reference to FIG. 1, one or more circulation devices 104 (one shown) may be positioned at one or more locations within the channel 102 to enable circulation (e.g., shown as arrows in FIG. 1, with the direction of the arrows being non-limiting) to prevent sedimentation of the contents of an algae water slurry cultivated within the channel 102. Typically, circulation device(s) 104 are located before one or more curved sections of raceway pond 100, but may be positioned at other locations provided that sufficient bulk liquid flow velocity is maintained. Examples of suitable circulation device(s) 104 include powered mechanical devices, such as paddlewheels, jet mixers, airlift pumps, mixing boards, and the like, which may be used singly or in combination within channel 102 of raceway pond 100.

During circulation of an algae water slurry within the channel 102, various debris may accumulate along the bottom and/or walls 102a of the channel 102 (e.g., blown dirt, precipitated ash from the algae slurry, and other detritus), particularly in areas of relatively low circulation or flow within the channel 102. Pond liners contain this debris within the interior of the channel 102 and over time, this built-up debris must be removed to ensure that the productivity of the cultivating algae is not compromised.

Natural, clay lined open cultivation vessels exist and can be advantageous in environments comprising natural clay deposits. However, many locations of interest for algae biofuel facilities lack such clay deposits. Moreover, clay lined ponds may suffer from percolation of a portion of the water within a circulating algae slurry into the ground. Percolation rates may be, for example, on the order of about 0.08 inches per day, requiring close watch of the algae slurry volume and replenishment, when appropriate, to carefully maintain the necessary growth conditions of the particular algae. Further, natural clay deposits may retain high ash content due to erosion of the interior bottom or walls of an open cultivation vessel and/or adjacent berm(s), which may dilute the algae slurry and/or interfere with downstream processing of algae cells into products of interest, such as biofuels.

Because natural liners may pose one or more of the above issues, open cultivation vessels are typically lined with a polymeric liner. Such polymeric liners may be made of natural or synthetic polymers such as, for example, linear low-density polyethylene (LLDPE), high-density polyethylene (HDPE), ethylene propylene diene monomer rubber (EPDM), polypropylene (PP), and chlorosulfonated polyethylene rubber (CSPE). Selection of the composition of a polymer liner may be based on a number of factors such as cost, compatibility of food grade cultivation techniques and/or standards, resistance to weathering, and the like, and any combination thereof. These typical liners are composed of a single material used at a single thickness (e.g., 60 mil). Accordingly, standard liners use a single material of a single thickness for lining all portions of open cultivation vessels, including the interior bottom, interior walls, and adjacent berms because standard open cultivation ponds are sized having a surface area of about one to two acres, which do not warrant optimization for multiple areas.

However, as discussed herein, scale-up requirements necessitate large-scale ponds of much greater surface area, and these large-scale ponds may have an area size on a magnitude of about 5 acres to about 30 acres, encompassing any value and subset therebetween (e.g., a 20 acre raceway pond may have a length of about 3,000 feet and a width of about 150 feet, which may depend on various factors such as land topography). In such instances, currently available polymeric liners are inadequate to sufficiently protect and service such large open cultivation ponds. For example, the thickness and/or material of current liners may be inadequate to prevent erosion of interior pond walls, inadequate to provide support for motorized vehicles to access interior portions of ponds for cleaning and maintenance (i.e., current liners generally only support foot traffic for manual pond cleaning and maintenance), and the like, and combinations thereof. That is, existent open cultivation liners are not designed for commercial, large-scale algae systems.

Figure 2A:
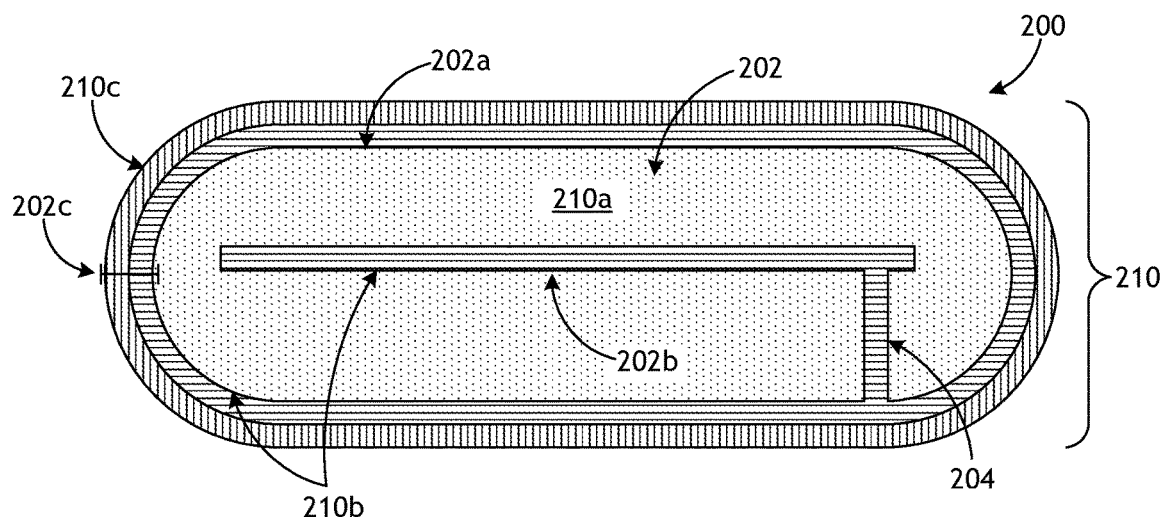
FIG. 2A is a schematic illustration of a top-view of a large-scale raceway pond open algae cultivation vessel comprising an optimized liner configuration according to one or more aspects of the present disclosure.
Figure 2B:
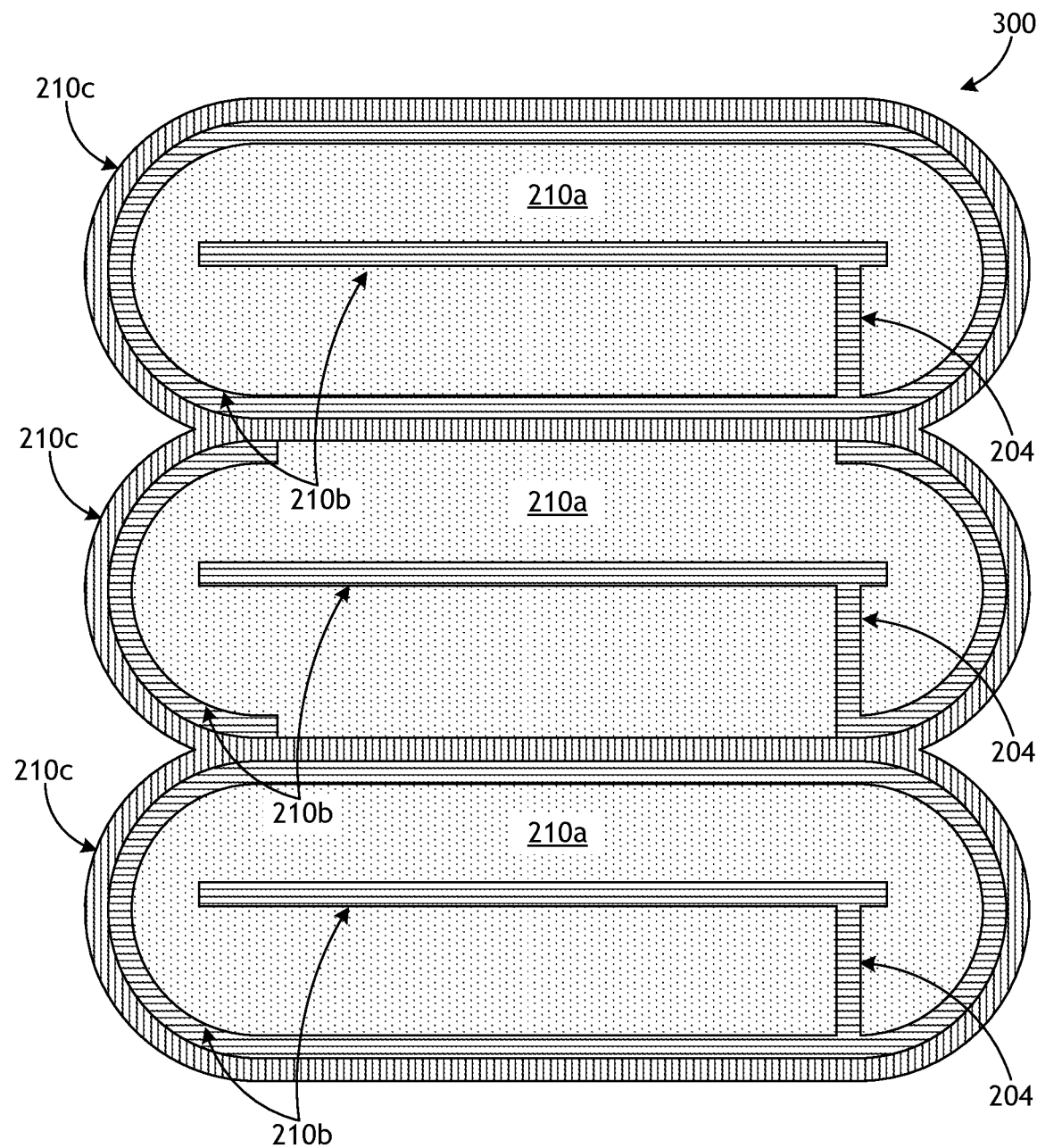
FIG. 2B is a schematic illustration of a top-view of a large-scale raceway pond open algae cultivation vessel comprising an optimized liner configuration according to one or more aspects of the present disclosure.

The present disclosure provides a combination of separate liners or integrated liners (made as part of a single, unified liner, such as by welding) to accommodate large-scale open cultivation systems to maximize effectiveness and, thus algae productivity, while minimizing operational costs, including where applicable, facility footprint size requirements. Referring now to FIGS. 2A and 2B, illustrated is a combination liner for use in any one of the large-scale ponds described herein, according to one or more aspects of the present disclosure. FIG. 2A represents a liner configuration for a single closed-loop, oval-shaped recirculation channel 200 (which may be equivalent in all or some respects to raceway pond 100 of FIG. 1, except for its size); FIG. 2B represents a liner configuration having multiple closed-loop, oval-shaped recirculation ponds (thus multiple channels). Where like elements are used in both FIG. 2A and FIG. 2B, like labels will be used.

Referring initially to FIG. 2A, raceway pond 200 is a single closed-loop, oval-shaped (e.g., pill-shaped) pond, represented as having recirculation channel 202, interior side walls 202a, separating divider 202b, and berm 202c (shown in two sections for ease of description of one or more aspects of a large-scale pond liner in accordance with the present disclosure). Accordingly, raceway pond 200 is represented as constructed from removed earthen material, thereby forming the resultant berm 202c. Liner 210 covers each of the recirculation channel 202, interior side walls 202a, separating divider 202b, and berm 202c. Liner 210 may be a combination of separate liner portions, and in one or more aspects, such portions may be, but need not be, welded or otherwise bonded together for ease of installation.

With continued reference to FIG. 2A, liner portion 210a (shown as dotted area) lines the majority of the recirculation channel 202. In some instances, liner portion 210a may also extend up toward including to the surface along the interior side walls 202a (toward or to the berm 202c) and/or extend up toward or to the surface of separating divider 202b, without departing from the scope of the present disclosure. Liner portion 210a has a minimum thickness to enclose and protect a circulating algae slurry, thereby minimizing costs without compromising integrity. In one or more aspects, the liner portion 210a may have a thickness in the range of about 10 mil to about 80 mil, encompassing any value and subset therebetween such as about 20 mil, or about 40 mil, or about 60 mil. For example, in some aspects, the liner portion 210a has a thickness of about 45 mil. The particular material for forming liner portion 210a is not considered to be particularly limited and may be any of the aforementioned polymeric materials (e.g., LLDPE, HDPE, EPDM, PP, CSPE, and the like). In one or more aspects, the liner portion 210a is composed of LLDPE.

Compared to liner portion 210a, the liner portions covering at least the surface of separating divider 202b and berm 202c are of a greater thickness to at least accommodate cleaning and maintenance needs of the pond 200. In one or more aspects, liner portion 210b (shown as horizontal striped area) lines at least the proximal portion of berm 202c relative to the interior side wall 202b and separating divider 202b, and optionally extending downward toward liner portion 210a, including contacting or otherwise welded (bonded) to liner portion 210a. Liner portion 201b has a thickness sufficient to support foot traffic, as well as vehicular access (e.g., gators, mules, ATVs, and the like) along the exterior and interior of the of pond 200 to allow for ease of cleaning and repair of such large-scaled areas. In one or more aspects, the liner portion 210b may have a thickness in the range of about 15 mil to about 200 mil, encompassing any value and subset therebetween, such as about 50 mil, or about 85 mil, or about 100 mil, or about 150 mil. The particular material for forming liner portion 210b is not considered to be particularly limited and may be any of the aforementioned polymeric materials (e.g., LLDPE, HDPE, EPDM, PP, CSPE, and the like). In one or more aspects, the liner portion 210b is composed of LLDPE.

As shown, liner 210b may be continuous between at least the proximate portion of berm 202c and at least the surface of separating divider 202b, which may be facilitated by use of an access way 204, which as shown is also covered or composed by liner 210b. All or a portion of the access way 204 may be composed of concrete or another structural material for supporting motor vehicles or may otherwise be composed solely of liner 210b. In one or more other aspects, a portion of the access way 204, such as that bridging over berm 202c, may be composed of concrete, whereas the remaining portion of access way 204 is composed of the separating divider 202b (i.e., solely a liner). In other aspects, access way 204 is not lined with liner 210b (thus the liner 210b is discontiguous between at least the proximate portion of berm 202c and at least the surface of separating divider 202b). In one or more aspects, to provide sufficient vehicular access to the pond 200, access way 204 has a width of about 10 feet to about 50 feet, encompassing any value and subset therebetween, such as about 15 feet, or about 20 feet, or about 30 feet. Access way 204 may additionally provide support for one or more circulation devices (e.g., circulation device 104 of FIG. 1).

Optionally, as shown, a distal portion of the berm 202c may be lined with liner portion 210c (shown as vertical striped area) that is optimized for weathering, particularly UV light exposure as this section does not benefit from any substantial protection given by the algae culture absorbing light rays. Moreover, the distal portion of the berm 202c, if sloped or otherwise formed from mounding dirt may require a higher mechanical strength liner due to frequent cleaning of bacterial cultures growing along the water's edge. In one or more aspects, the optional liner portion 210c may have a thickness in the range of about 15 mil to about 80 mil, encompassing any value and subset therebetween, such as about 20 mil, or about 40 mil, or about 60 mil. The particular material for forming liner portion 210c is not considered to be particularly limited and may be any of the aforementioned polymeric materials (e.g., LLDPE, HDPE, EPDM, PP, CSPE, and the like). In one or more aspects, the liner portion 210c is composed of LLDPE.

It is to be appreciated that any of liner 210a, 210b, and optional 210c may be composed of the same or different polymeric material, without departing from the scope of the present disclosure. In preferred embodiments, each portion of liner 210 is composed of the same material (e.g., LLDPE or other polyethylene material), which may facilitate ease of manufacture, ease of welding (bonding), and the like.

Accordingly, the present disclosure provides a joined liner (e.g., a welded liner) that comprises at least two thickness portions (e.g., liner 210a and 210b), a thinner liner portion and a thicker liner portion. In one or more aspects, the thicker portion is at least about 1.5 times thicker than the thinner portion, generally in the range of at least 1.5 times thicker to about 5 times thicker, encompassing any value and subset therebetween. Moreover, the thicker portion of the liner typically takes up no more than about 30% of the entire pond liner area, generally in the range of lesser than about 30% to about 5%, encompassing any value and subset therebetween.

FIG. 2B represents a raceway pond system 300 having multiple side-by-side (adjacent) ponds, each having liner portions 210a, 210b, and 210c and access ways 204 (as described above with reference to FIG. 2A, and thus will not be described again with reference to FIG. 2B). In one or more aspects, the liners described herein may allow significant scale-up advantage by placing two or more ponds (three shown in FIG. 2B) side-by-side. Indeed, the liners permit sharing of berms (e.g., having one or both of liner 210b and 210c) between adjacent individual ponds; as shown, interior pond of pond system 300 shares berms liners 210a and 210b along its side edges with each of the adjacent ponds. Because these berm liners support vehicular access, the need for roads between each large-scale pond (e.g., 20 acre ponds) is negated and costs associated with pipelines and electrical lines can also be reduced. As such, a greater number of ponds can be included in a single facility based on the configuration (and liner(s)) described herein.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more elements are presented herein. Not all features of a physical implementation are described or shown in this application for the sake of clarity. It is understood that in the development of a physical embodiment incorporating one or more elements of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

The present disclosure provides, among others, the following aspects, each of which may be considered as optionally including any alternate thereof.

Clause 1: A joined liner for lining an open algae cultivation vessel, wherein the liner comprises a first portion having a first thickness and a second portion comprising a second thickness, wherein the second thickness is at least about 1.5 times greater than the first thickness.

Clause 2: The liner of Clause 1, wherein the first portion lines at least a portion of a recirculation channel of the open algae cultivation vessel and the second portion lines at least a first portion of a berm adjacent to the recirculation channel.

Clause 3: The liner of Clause 1 or Clause 2, wherein the first thickness is in the range of about 10 mil to about 80 mil.

Clause 4: The liner of any of the preceding Clauses, wherein the second thickness is in the range of about 15 mil to about 200 mil.

Clause 5: The liner of any of the preceding Clauses, wherein the first portion and the second portion are composed of different polymeric materials.

Clause 6: The liner of Clause 5, wherein the polymeric materials are one of linear low-density polyethylene, high-density polyethylene, ethylene propylene diene monomer rubber, polypropylene, or chlorosulfonated polyethylene rubber.

Clause 7: The liner of Clause 6, wherein one of the first portion or the second portion is composed of linear low-density polyethylene.

Clause 8: The liner of any of Clause 1 to Clause 4, wherein the first portion and the second portion are composed of identical polymeric materials.

Clause 9: The liner of Clause 8, wherein the polymeric materials are one of linear low-density polyethylene, high-density polyethylene, ethylene propylene diene monomer rubber, polypropylene, or chlorosulfonated polyethylene rubber.

Clause 10: The liner of Clause 9, wherein the polymeric material is linear low-density polyethylene.

Clause 11: A system comprising: an open algae cultivation vessel; and the liner of any of the preceding Clauses.

Clause 12: A method comprising: cultivating an algae water slurry within an open algae cultivation vessel, the open algae cultivation vessel lined with the liner of any of Clause 1 to Clause 10.

Clause 13: A joined liner for lining an open algae cultivation vessel, wherein the liner comprises a first portion having a first thickness, a second portion comprising a second thickness, and a third portion comprising a third thickness, wherein the first thickness, the second thickness, and the third thickness are different, and wherein the second thickness is at least about 1.5 times greater than the first thickness.

Clause 14: The liner of Clause 13, wherein the first portion lines at least a portion of a recirculation channel of the open algae cultivation vessel, the second portion lines a first portion of a berm adjacent to the recirculation channel, and the third portion lines at least a second portion of the berm adjacent to the first portion of the berm and distal to the recirculation channel.

Clause 15: The liner of Clause 13 or Clause 14, wherein the first thickness is in the range of about 10 mil to about 80 mil.

Clause 16: The liner of any of Clause 13 to Clause 15, wherein the second thickness is in the range of about 15 mil to about 200 mil.

Clause 17: The liner of any of Clause 13 to Clause 16, wherein the third thickness is in the range of about 15 mil to about 80 mil.

Clause 18: The liner of any of Clause 13 to Clause 17, wherein the first portion, second portion, and third portion are composed of different polymeric materials.

Clause 19: The liner of Clause 18, wherein the polymeric materials are one of linear low-density polyethylene, high-density polyethylene, ethylene propylene diene monomer rubber, polypropylene, or chlorosulfonated polyethylene rubber.

Clause 20: The liner of Clause 19, wherein one of the first portion, the second portion, or the third portion is composed of linear low-density polyethylene Clause 21: The liner of any of Clause 13 to Clause 17, wherein the first portion, second portion, and third portion are composed of identical polymeric materials.

Clause 22: The liner of Clause 21, wherein the polymeric materials are one of linear low-density polyethylene, high-density polyethylene, ethylene propylene diene monomer rubber, polypropylene, or chlorosulfonated polyethylene rubber.

Clause 23: The liner of Clause 22, wherein the polymeric material is linear low-density polyethylene.

Clause 24: A system comprising: an open algae cultivation vessel; and the liner of any of Clause 13 to Clause 23.

Clause 25: A method comprising: cultivating an algae water slurry within an open algae cultivation vessel, the open algae cultivation vessel lined with the liner of any of Clause 13 to Clause 23.

Therefore, the aspects of the methods and systems presented herein are well adapted to attain the ends and advantages mentioned as well as those that are inherent therein. The particular examples and configurations disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present disclosure. The aspects illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A joined liner for lining an open algae cultivation vessel, wherein the liner comprises a first portion joined to a second portion, the second portion joined to a third portion, the first portion lining only a first area of the open algae cultivation vessel corresponding to a bottom surface and at least a portion of an interior side wall defining a recirculation channel of the open algae cultivation vessel, the second portion lining only a second area of the open algae cultivation vessel corresponding to at least a surface of a separating divider positioned within the recirculation channel and a proximal portion of a berm contiguous with the interior side wall, and the third portion lining only a third area of the open algae cultivation vessel corresponding to a distal portion of the berm, the first portion comprising a first thickness and the second portion comprising a second thickness and the third portion comprising a third thickness, and wherein the first thickness, the second thickness, and the third thickness are different.

2. The liner of claim 1, wherein the first area corresponds to the bottom surface and a majority of the interior side wall of the recirculation channel of the open algae cultivation vessel.

3. The liner of claim 1, wherein the first thickness is in a range of about 10 mil to about 80 mil.

4. The liner of claim 1, wherein the second thickness is in a range of about 15 mil to about 200 mil.

5. The liner of claim 1, wherein the first portion and the second portion are composed of different polymeric materials.

6. The liner of claim 5, wherein the polymeric materials are one of linear low-density polyethylene, high-density polyethylene, ethylene propylene diene monomer rubber, polypropylene, and chlorosulfonated polyethylene rubber.

7. The liner of claim 1, wherein the second portion lines about 5% to 30% of the open algae cultivation vessel.

8. The liner of claim 1, wherein the first portion and the second portion are composed of identical polymeric materials.

9. The liner of claim 8, wherein the polymeric materials are one of linear low-density polyethylene, high-density polyethylene, ethylene propylene diene monomer rubber, polypropylene, or chlorosulfonated polyethylene rubber.

10. The liner of claim 9, wherein the polymeric material is linear low-density polyethylene.

11. A joined liner for lining an open algae cultivation vessel, wherein the liner comprises a first portion joined to a second portion, the second portion joined to a third portion, the first portion lining only a first area of the open algae cultivation vessel, the second portion lining only a second area of the open algae cultivation vessel, and the third portion lining only a third area of the open algae cultivation vessel, the first portion having a first thickness, the second portion comprising a second thickness, and the third portion comprising a third thickness,
    wherein the first thickness, the second thickness, and the third thickness are different, and
    wherein the second thickness is at least about 1.5 times greater than the first thickness.

12. The liner of claim 11, wherein the first portion lines at least a portion of a recirculation channel of the open algae cultivation vessel, the second portion lines a first portion of a berm adjacent to the recirculation channel, and the third portion lines at least a second portion of the berm adjacent to the first portion of the berm and distal to the recirculation channel, wherein the third portion is configured to be resistant to weathering and UV light exposure.

13. The liner of claim 11, wherein the first thickness is in a range of about 11 mil to about 80 mil, the second thickness is in a range of about 76 mil to about 200 mil, and the third thickness is in a range of about 16 to about 80 mil.

14. The liner of claim 11, wherein the first portion, second portion, and third portion are composed of different polymeric materials.

15. The liner of claim 11, wherein the open algae cultivation vessel comprises a recirculation channel, a separating divider, and an exterior berm, wherein the first portion lines at least a portion of the recirculation channel of the open algae cultivation vessel, the second portion lines a first portion of the berm adjacent to the recirculation channel.

16. The liner of claim 11, wherein the first portion, second portion, and third portion are composed of identical polymeric materials.

17. The liner of claim 16, wherein the polymeric materials are one of linear low-density polyethylene, high-density polyethylene, ethylene propylene diene monomer rubber, polypropylene, or chlorosulfonated polyethylene rubber.

18. The liner of claim 17, wherein the polymeric material is linear low-density polyethylene.

* * * * *